United States Patent [19]

Gozes et al.

[11] Patent Number: 5,147,855
[45] Date of Patent: Sep. 15, 1992

[54] CONJUGATES OF VIP AND ACTIVE FRAGMENTS THEREOF WITH HYDROPHOBIC MOIETIES AND TOPICAL COMPOSITIONS FOR MALE IMPOTENCE

[75] Inventors: Illana Gozes, Ness Ziona; Matityahu Fridkin, Rehovot, both of Israel

[73] Assignee: Yeda Research and Development Co. Ltd., Rehovot, Israel

[21] Appl. No.: 376,559

[22] Filed: Jul. 7, 1989

[30] Foreign Application Priority Data

Jul. 8, 1988 [IL] Israel .................................. 87055

[51] Int. Cl.$^5$ ..................... C07K 7/10; C07K 7/08; A61K 37/02
[52] U.S. Cl. ..................................... 514/12; 514/14; 530/324; 530/327
[58] Field of Search ................. 530/324, 313, 327; 514/12, 14

[56] References Cited

U.S. PATENT DOCUMENTS

| | | | |
|---|---|---|---|
| 3,879,371 | 4/1975 | Said et al. | |
| 4,605,641 | 8/1986 | Bolin et al. | |
| 4,853,371 | 8/1989 | Coy et al. | 514/12 |
| 4,885,164 | 12/1989 | Thurow | 424/85.4 |
| 4,935,491 | 6/1990 | Folkers et al. | 530/313 |
| 4,935,492 | 6/1990 | Lewicki et al. | 530/324 |
| 4,939,224 | 7/1990 | Musso et al. | 530/324 |

FOREIGN PATENT DOCUMENTS

| | | |
|---|---|---|
| 0225639 | 8/1987 | European Pat. Off. |
| 0297068 | 12/1988 | European Pat. Off. |

OTHER PUBLICATIONS

Vasoactive Intestinal Polypeptide and the Reproductive System Annals of New York Academy of Sciences, 1988; 393–404; Fahrenkrug et al.

Octapeptides Deduced From the Neuropeptide Receptor-like Pattern of Antigen T4 in Brain Potently Inhibit Human Immunodeficiency . . . Infectivity, vol. 83, pp. 9254–9258 (1986); Pert et al.

Solid Phase Peptide Synthesis, vol. 85, pp. 2149–2154 R. B. Merrifield (1963).

Attenuation by a 5x-Reductase Inhibitor of the Activational Effect of Testosterone Propionate on Penile Erections in Castrated Male Rats, vol. 109, No. 4, pp. 1047–1051 (1981), Bradshaw et al.

Effects of Chronic Hyperprolactinemia on Sexual Arousal and Erectile Function in Male Rats Neuroendocrinology 42:368–375 (1986), Doherthy et al.

Jan Fahrenkrug et al., Vasoactive Intestinal Polypeptide and the Reproductive System, 1988, Annals of New York Academy of Sciences, (393–404).

*Primary Examiner*—Lester L. Lee
*Assistant Examiner*—A. M. Davenport
*Attorney, Agent, or Firm*—Browdy and Neimark

[57] ABSTRACT

There are provided pharmaceutical compositions for topical transdermal application for the treatment of male impotence. The active ingredients of such compositions are selected from vasoactive intestinal peptide (VIP), effective derivatives thereof and effective fragments thereof. In the compositions for the treatment of male impotence a transdermally effective conjugate of VIP, its derivatives or fragments coupled to a hydrophogic moiety, is used.

8 Claims, No Drawings

CONJUGATES OF VIP AND ACTIVE FRAGMENTS THEREOF WITH HYDROPHOBIC MOIETIES AND TOPICAL COMPOSITIONS FOR MALE IMPOTENCE

FIELD OF THE INVENTION

The invention relates to pharmaceutical compositions for the treatment of male impotence. The transdermal application of vasoactive intestinal peptide (VIP) derivatives or fragments thereof, coupled to a suitable hydrophobic moiety, enhances sexual activity.

The active ingredient is VIP, functional derivatives thereof, active fragments thereof, and modified peptides wherein one or more of the amino acids are substituted by others. The backbone of the compositions is a naturally occurring material, or derivative thereof.

BACKGROUND OF THE INVENTION

Impotence, a condition that can bring much suffering to the life of the afflicted individual and those surrounding him, can be caused by psychological as well as organic problems. It is estimated that in the United States alone, 10 million men suffer from varying degrees of impotence. In general, impotence is a predominant syndrome affecting at least 10-15% of the male population. In men above 40 years of age, the occurrence of impotence is prevalent due to neuroendocrine failures associated with aging, and any man over the age of 40 years may experience occasional impotence. The mechanism of penile erection is a complicated one and requires the intactness of the endocrine system, the nervous system and the vascular system. Many times the suffering individual is hesitant to seek medical help and at the moment the remedies available to the physician are rather limited. Organic abnormalities can be treated by surgery and implantations. Erection was also obtained by injection of smooth muscle relaxants such as phenoxybenzamine. It is, of course, quite understandable that superior treatment is needed and the invention relates to an ointment to treat impotence.

SUMMARY OF THE INVENTION

The invention relates to pharmaceutical compositions for the treatment of male impotence. The transdermal application of vasoactive intestinal peptide (VIP) or derivatives or fragments thereof, coupled to a suitable hydrophobic moiety, enhances sexual activity.

The active ingredient are VIP, functional derivatives thereof, active fragments thereof, and modified peptides wherein one or more of the amino acids are substituted by others. The backbone of the compositions is a naturally occuring material, or derivative thereof.

The peptide of interest, Vasoactive Intestinal Peptide (VIP) fulfils several of the chemical criteria for a neurotransmitter in penile erection in the male: it is present in nerve fibers with nerve endings around cavernous smooth muscle and blood vessels and it is elevated during erection. Moreover, injection of exogenous VIP induces erection in man. It is important to add that in impotent men it was unequivocally shown that VIP quantities decrease locally in their penises. Since VIP was found to be a key neurotransmitter in erection formation, its local administration should help to relieve the dysfunction. Past studies used local VIP injection into the penis as the mode of drug administration. Using an animal model, we developed an ointment containing modified VIP which enhances mating behaviour in mammals, as evident from experiments with rats. Thus the invention relates to a pharmaceutical composition for the treatment of male impotence, for topical application, which composition contains as active ingredient a transdermally effective conjugate which comprises on the one hand vasoactive intestinal peptide (VIP), or an effective derivative thereof, or an effective fragment thereof, and on the other hand a hydrophobic moiety to which same is coupled.

The behavioural model for studies of sexual behaviour was the castrated rat model. Castrated rats lose their sexual activity in a time dependent manner and we used this characteristic to develop a model for investigating the therapeutic activity of VIP.

The sequence of VIP, a 28-amino acid peptide, is as follows:

$$\overset{1}{\text{—His—Ser—Asp—Ala—Val—Phe—Thr—Asp—Asn—Tyr—Thr—Arg—}}^{7}$$

$$\overset{16}{\text{—Leu—Arg—Lys—Gln—Met—Ala—Val—Lys—Lys—Tyr—Leu—Asn—}}$$

$$\overset{28}{\text{—Ser—Ile—Leu—Asn—NH}_2.}$$

The peptide chain was assembled according to the solid-phase methodology (Merrifield (1963) J. Am. Chem. Soc. 85:2149). Partial sequences were also synthesized by this approach.

The following hydrophobic derivatives of VIP were prepared by attaching, as the last coupling step, a long chain aliphatic carboxylic acid to the N-terminus of the peptide chain. This was accomplished while the peptide was still attached to the polymeric support:

1. $CH_3(CH_2)_6CO-VIP$
2. $CH_3(CH_2)_{16}CO-VIP$
3. $CH_3(CH_2)_{16}CO-VIP_{7-28}$
4. $CH_3(CH_2)_{16}CO-VIP_{16-28}$
5. 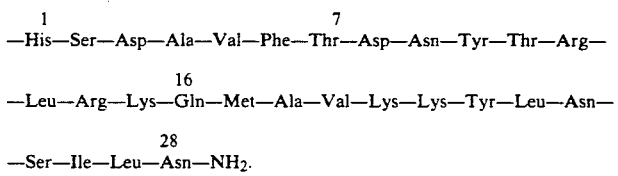

The following peptides were prepared by aminolysis of peptide-polymer conjungates with long-chain aliphatic amines; chain extension occurs at the C-terminus of the VIP:
1. VIP-CONH $CH_2CH_3$
2. VIP-CONH$(CH_2)_3CH_3$
3. VIP-CONH$(CH_2)_7CH_3$ All peptides were purified by HPLC and characterized by their amino acid analysis.

The following examples are to be construed in a nonlimitative manner.

EXAMPLES

Synthesis of Stearyl-VIP

Synthesis was carried out via the solid-phase strategy. All amino acid derivatives were purchased from Peptide Institute Inc. (Japan). It was performed either automatically using Peptide Synthesizer (Applied Biosystem) or manually. α-amino functional groups were protected by t-butyloxycarbonyl (t-Boc). Side chain protecting groups were as follows: His, $N^{im}$-p-toluenesulfonyl; Lys, 2-chlorobenzyloxycarbonyl; p Tyr, O-2.6-dichlorobenzyl; Arg, $N^G$-p-toluenesulfonyl; Asp, β-benzyl; Thr and Ser, O-benzyl. The first amino acid (Asn) was attached to benzhydryl amine resin (Chemalog) using N.N'-dicyclohexylcarbodiimide (DCC) as a coupling agent. All coupling stages were performed with a threefold excess of protected amino acid derivatives using DCC and 1-hydroxylbenzotriazole (HOBt) as coupling agents. All stages of coupling were monitored with ninhydrin. The stearic acid residue was added similarly to amino acid residues using DCC/HOBt. Final cleavage of the peptide from the polymeric support along with deprotection was achieved with anhydrous HF. The product was first purified by gel-filtration on a Sephadex G-25 column followed by HPLC on reversed phase $C_{18}$-column using a linear gradient obtained by mixing (A) 0.1% trifluoroacetic acid (TFA) in water and (B) 0.1% TFA in 70% acetonitrile and 30% water. The product gave, after acidic hydrolysis, the expected ratio of its constituent amino acids.

Other peptides were similarly prepared.

It is clear that introduction of hydrophobic moieties into the peptide chain of VIP can also take place within the chain, e.g., at the amino side chains of Lys. The hydrophobic moieties can be aliphatic, linear saturated (as in the compounds prepared), linear unsaturated (containing double or triple bonds), branched, saturated and unsaturated, linear and branched containing heteroatoms, aromatic-aliphatic or aromatic, be introduced into either C, N terminus or within the peptide chain, or at two or more positions. All these modifications can be performed on fragments of VIP as well, or on any other biologically active analog of VIP.

The animal model — All tested rats (Wistar derived from the departmental colony, Hormone Research Department, at the Weizmann Institute of Science), are sexually experienced male rats around 3 months of age (body weight ~250 g). At this age, the rats are castrated by removal of the testes and injected daily with testosterone for at least 14 consecutive days.

All rats (males and females) that take part in the experiment are kept in a 12-hour light 12-hour dark cycle. Prior to testing, each male is put in a separate cage for at least 1 hour. A sexually receptive female is introduced to each male. Females were tested for their receptivity by vaginal smearings. The latencies of mounts and intromissions are recorded. The tests are terminated if the male does not mount within 15 minutes. Using castrated animals we achieved decreased sexual activity which is expressed by longer intervals between intromissions and less intromissions during the 15 min observation periods.

Initially, we tested a few VIP analogs by injection (intravenously 5–10 μg/animal). As a control we injected saline at identical volumes (5–10 μl).

Table 1 shows the results for stearyl-VIP injection. At the upper left side of the chart we see that stearyl-VIP potentiates sexual activity in a comparable manner to VIP (right hand side of the table). This analog is lipophylic and hence may be a candidate for topical application.

As we have obtained positive results with stearyl-VIP by injection we have now developed a topical application method. This was achieved by mixing 20 μl of 1 μg/ml VIP-stearyl with 10 μl dimethyl sulfoxide (DMSO) and direct topical application on the sex organ. In Table II one can easily notice a remarkable sexual arousal after stearyl-VIP application compared with control rats subjected to DMSO. We therefore suggest that stearyl-VIP could be used as a potentiator of sexual activity in animals.

In Table III we compare the topical application of the carrier (DMSO) to stearic acid by itself, to VIP by itself and to stearyl-VIP. It is self-evident that stearyl-VIP is the most active analog. A shorter (8 amino acid) VIP analog which is related to the human immunodeficiency virus (peptide T) which did not show much activity upon topical application by itself is somewhat active in a conjugated form but not as VIP-stearyl.

(A) The effect of topical application of stearyl-VIP on the sexual behaviour of male rats are summarized in Table IV.

Preparation of Ointment — Lanolin (1 g), water (3 g) DMSO (7 drops) and 10 mg of stearyl-VIP were manually homogenized in a mortar. An amount of paste, containing 30–50 μg peptide was applied onto the rat's penis and sexual behaviour, following the methodology previously described, was monitored. As shown in the Table, the peptide showed about 25% decrease in intromission latency and two-fold increase in ejaculations in 10 animals.

(B) Using the same protocol as in (A) an ointment of VIP-oleyl was prepared and tested. It did show a certain effect in shortening of intromission latency (~10%) and also increased, though much less than stearyl-VIP, number of ejaculations.

The effective dose for humans is between 1 and 50 μg.

We claim that VIP-stearyl can be used in topical application to improve mammalian sexual behaviour in sexually deficient males. Moreover, we claim that further modification using the same idea of a lypophylic derivative may even improve the material as VIP is known to be a bronchodilator as well as a vasodilator. Other therapeutical applications such as in asthma and blood pressure regulation are also claimed.

LEGENDS TO TABLES

Table I

Rats were castrated and injected daily for 15 consecutive days with testosterone at 4 μg/100 g body weight (BW). Tests were performed with stearyl-VIP or VIP at 10 μg/animal.

Table II

Rats were castrated and injected daily for 16 consecutive days with testosterone at 2 μg/100 g BW. Testing was performed by topical application of stearyl-VIP-20 μg/20 μl mixed with 10 μl DMSO and compared to topical application of 30 μl DMSO.

Table III 6 rats, 120 days old, sexually experienced, were tested. The rats were castrated 14 days earlier and were injected with 4 μg/100 g BW of testosterone daily. In the table we see an increase in number of intromissions and shortening of latency after topical application of HIV Pep T-stearyl and stearyl-VIP. All 6 materials were tested by topical application. Also there is a clear increase in the number of ejaculations after applications of HIV-Pep T-stearyl and stearyl-VIP. Corresponding results are expected with human males.

Table IV

Summary of the effect of topical application of stearyl-VIP on the sexual behaviour of male rats.

TABLE I

| | Saline | VIP stearyl | | Saline | | VIP | |
|---|---|---|---|---|---|---|---|
| Rat | Obs. | Intromission latency (seconds) | Obs. | Intromission latency | Rat | Obs. | Intromission latency | Obs. | Intromission latency |
| G | 10 | 71 ± 14:E | 7(1M) | 28 ± 7:E | A | 9 | 41 ± 2 | 26 | 30 ± 5:E |
| | | | 4 | 50 ± 17:E | $A_1$ | 9 | 54 ± 4:E | 15 | 27 ± 7:E |
| $G_1$ | 11(1M) | 54 ± 9 | 12(1M) | 33 ± 6:E | $A_2$ | 6 | 38 ± 2 | 19 | 22 ± 2:E |
| $G_2$ | 23(8M) | 30 ± 4 | 20(7M) | 37 ± 6:E | B | 9 | 59 ± 6 | 10 | 56 ± 10:E |
| $F_1$ | 10(3M) | 78 ± 20:E | 14 | 56 ± 8:E | | | | | |
| $F_3$ | 2 | 101 ± 21:E | 6 | 45 ± 7:E | $B_2$ | 4 | 50 ± 5 | 13 | 26 ± 6:E |
| F | 9 | 38 ± 7:E | 7(4M) | 17 ± 3:E | | | | | |
| | 3 | 13 ± 6 | | | | | | | |

Obs. = Number of intromissons per 15 minute test period.
E = Ejaculations
M = Mountings without intromission

TABLE II

TOPICAL APPLICATION

| | DMSO | | Stearyl-VIP | |
|---|---|---|---|---|
| Rat | Obs. | Intromission latency | Obs. | Intromission latency |
| $A_1$ | 11 | 48 ± 12 | 21 | 23 ± 4 |
| $A_2$ | 8 | 79 ± 30 | 14 | 29 ± 4 |
| $A_3$ | — | — | 14 | 32 ± 8 |
| B | 21 | 31 ± 5:E | 10 | 16 ± 3:E |
| | | | 3 | 38 ± 10 |
| $B_2$ | — | — | 11(3M) | 18 ± 7 |
| $B_3$ | 12 | 54 ± 12 | 25 | 24 ± 4 |

Please note that rats $B_2$ and $A_3$ were sexually active only after Stearyl-VIP application.

TABLE III

| | DMSO | | HIV-PEPT Stearyl | | Stearic acid | | Stearyl VIP | | VIP | |
|---|---|---|---|---|---|---|---|---|---|---|
| Rat | No. Ob. | Int. Latency | No. Ob. | Int. Latency | No. Ob. | Int. Latency | No. Ob. | Int. Latency | No. Ob. | Int. Latency |
| A | — | — | — | — | — | — | 6 | 66 ± 15 | — | — |
| B | 24 | 29 ± 6E | 21 | 23 ± 3E | 19 | 26 ± 1E | 28 | 18 ± 3E | 21 | 22 ± 6 |
| C | 11 | 67 ± 3E | 16 | 28 ± 2E | 21 | 18 ± 3E | 20 | 18 ± 2E | 15 | 20 ± 1 |
| $A_1$ | — | — | — | — | — | — | — | — | — | — |
| $B_1$ | 6 | 104 ± 10 | 12 | 46 ± 2 | 19 | 36 ± 2E | 49 | 12 ± 3E | 10 | 59 ± 3 |
| $C_1$ | 15 | 45 ± 2 | 28 | 29 ± 4E | — | — | 31 | 26 ± 1E | — | — |

TABLE IV

The affect of stearyl-VIP on sexual behaviour of male rats

| | No treatment | | | | | | control ointment | | |
|---|---|---|---|---|---|---|---|---|---|
| | Exp. 1 | | Exp. 2 | | Exp. 3 | | Exp. 1 | | Exp. 2 |
| RATS | Obs. | I.L. | Obs. | I.L. | Obs. | I.L. | Obs. | I.L. | Obs. |
| 1 | 9 | 40 ± 1 | 10 | 39 ± 5 | 13 | 30 ± 7:E | 12 | 32 ± 3:E | 13 |
| 2 | 15 | 25 ± 2 | 11 | 39 ± 9 | 12 | 36 ± 5:E | 12 | 30 ± 1 | 11 |
| 3 | 10 | 40 ± 5 | 9 | 45 ± 5 | 12 | 37 ± 3:E | 13 | 26 ± 4:E | 14 |
| 4 | 11 | 37 ± 5 | 9 | 41 ± 3 | 9 | 42 ± 5 | 10 | 40 ± 5 | 11 |
| 5 | 13 | 30 ± 2 | 10 | 39 ± 5 | 10 | 40 ± 7 | 11 | 36 ± 3 | 12 |
| 6 | 11 | 36 ± 3:E | 14 | 31 ± 7:E | 13 | 32 ± 6:E | 13 | 33 ± 2 | 14 |
| 7 | 17 | 20 ± 6:E | 13 | 30 ± 5:E | 15 | 27 ± 3:E | 14 | 29 ± 1 | 12 |
| 8 | 9 | 40 ± 7 | 10 | 41 ± 6 | 9 | 42 ± 3 | 11 | 39 ± 3 | 12 |
| 9 | 8 | 42 ± 3 | 11 | 38 ± 5 | 12 | 37 ± 4:E | 13 | 29 ± 6:E | 12 |
| 10 | 14 | 27 ± 5:E | 13 | 33 ± 3 | 14 | 28 ± 3:E | 13 | 31 ± 1 | 14 |

| | control ointment | | | | stearyl-VIP ointment | | | | | |
|---|---|---|---|---|---|---|---|---|---|---|
| | Exp. 2 | | Exp. 3 | | Exp. 1 | | Exp. 2 | | Exp. 3 | |
| RATS | I.L. | | Obs. | I.L. | Obs. | I.L. | Obs. | I.L. | Obs. | I.L. |
| 1 | 30 ± 3 | | 11 | 44 ± 3 | 12 | 36 ± 3:E | 13 | 30 ± 3:E | 11 | 40 ± 4:E |
| 2 | 36 ± 5:E | | 10 | 47 ± 2 | 11 | 32 ± 5 | 11 | 40 ± 3:E | 12 | 36 ± 5:E |
| 3 | 24 ± 2 | | 12 | 41 ± 5 | 12 | 29 ± 4 | 12 | 39 ± 4:E | 11 | 39 ± 3:E |
| 4 | 39 ± 6 | | 10 | 46 ± 3 | 11 | 28 ± 5:E | 10 | 37 ± 5:E | 11 | 23 ± 4:E |
| 5 | 37 ± 2 | | 11 | 40 ± 2 | 9 | 46 ± 4:E | 11 | 46 ± 2:E | 13 | 20 ± 5:E |
| 6 | 28 ± 3:E | | 12 | 38 ± 4 | 11 | 44 ± 2:E | 10 | 50 ± 3:E | 11 | 40 ± 1:E |
| 7 | 36 ± 5 | | 15 | 22 ± 5 | 12 | 39 ± 5:E | 11 | 41 ± 3:E | 14 | 22 ± 7:E |
| 8 | 32 ± 3 | | 16 | 16 ± 4 | 13 | 39 ± 1:E | 12 | 39 ± 3:E | 10 | 40 ± 3:E |
| 9 | 36 ± 2:E | | 12 | 32 ± 3:E | 10 | 48 ± 4:E | 11 | 46 ± 4:E | 9 | 40 ± 7:E |

TABLE IV-continued

The affect of stearyl-VIP on sexual behaviour of male rats

| 10 | 26 ± 2 | 14 | 22 ± 5 | 12 | 26 ± 3:E | 12 | 27 ± 4:E | 13 | 20 ± 2:E |

I.L. = Intermission Latency (sec)
E = Ejaculations

We claim:

1. A transdermally effective pharmaceutical composition for topical application for the treatment of male impotence which comprises as active ingredient a physiologically effective quantity of a conjugate of vasoactive intestinal peptide (VIP) or an active fragment thereof, said active fragment having activity whereby injection of such fragment induces erection in a man, coupled to a hydrophobic moiety.

2. A conjugate of an hydrophobic moiety of the formula $CH_3(CH_2)_nCO$, wherein n is an integer from 6 to 16, attached to the N-terminus of vasoactive intestinal peptide (VIP) molecule or a fragment which is the $VIP_{7-28}$ fragment or the $VIP_{16-28}$ fragment.

3. A conjugate of vasoactive intestinal peptide (VIP), or of an active fragment thereof, said active fragment having activity that injection of such fragment induces erection in a man, coupled through an N-terminus thereof to an hydrophobic moiety of the formula R-CO-, wherein R is a saturated or unsaturated aliphatic chain of 4 to 17 carbon atoms.

4. Stearyl-VIP conjugate of the formula:

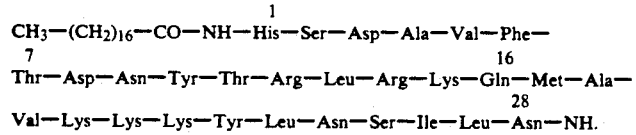

5. Stearyl-$VIP_{7-28}$ fragment conjugate of the formula:

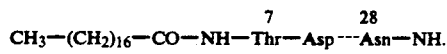

6. Stearyl-$VIP_{16-28}$ fragment conjugate of the formula:

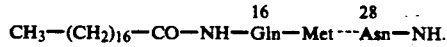

7. A transdermally effective pharmaceutical composition for topical application for the treatment of male impotence which comprises as active ingredient a physiologically effective quantity of a conjugate as claimed in claim 4.

8. A transdermally effective pharmaceutical composition for topical application for the treatment of male impotence which comprises as active ingredient a physiologically effective quantity of a conjugate as claimed in claim 5.

* * * * *